(12) United States Patent
Danielsson et al.

(10) Patent No.: US 9,358,404 B2
(45) Date of Patent: Jun. 7, 2016

(54) EFFECTIVE VOLUME FILLING WITH TEMPLATES

(75) Inventors: Karl Danielsson, Järfälla (SE); Håkan Nordström, Sollentuna (SE); Björn Somell, Stockholm (SE); Pär Lidberg, Vallentuna (SE)

(73) Assignee: ELEKTA AB (PUBL), Stockholm (SE)

( * ) Notice: Subject to any disclaimer, the term of this patent is extended or adjusted under 35 U.S.C. 154(b) by 566 days.

(21) Appl. No.: 13/518,329

(22) PCT Filed: Dec. 22, 2009

(86) PCT No.: PCT/EP2009/067809
§ 371 (c)(1),
(2), (4) Date: Aug. 29, 2012

(87) PCT Pub. No.: WO2011/076271
PCT Pub. Date: Jun. 30, 2011

(65) Prior Publication Data
US 2012/0316377 A1    Dec. 13, 2012

(51) Int. Cl.
*A61N 5/10*    (2006.01)

(52) U.S. Cl.
CPC ............... *A61N 5/103* (2013.01); *A61N 5/1031* (2013.01)

(58) Field of Classification Search
CPC ....... A61N 5/10; A61N 5/103; A61N 5/1031; A61N 2005/1034
USPC ................................................ 600/1; 378/65
See application file for complete search history.

(56) References Cited

U.S. PATENT DOCUMENTS

| | | | | |
|---|---|---|---|---|
| 5,373,844 A | * | 12/1994 | Smith et al. | 600/427 |
| 6,201,988 B1 | * | 3/2001 | Bourland et al. | 600/427 |
| 2008/0298550 A1 | | 12/2008 | Otto | |

FOREIGN PATENT DOCUMENTS

| WO | WO 2005/035061 A2 | 4/2005 |
|---|---|---|
| WO | WO 2005/072825 A1 | 8/2005 |

OTHER PUBLICATIONS

S. Jitprapaikulsarn, "An Optimization-Based Treatment Planner for Gamma Knife Radiosurgery", May 2005, retrieved at https://etd.ohiolink.edu/!etd.send_file?accession=case1109959500&disposition=inline on Aug. 27, 2014.*

* cited by examiner

*Primary Examiner* — Charles A Marmor, II
*Assistant Examiner* — Thaddeus Cox
(74) *Attorney, Agent, or Firm* — Birch, Stewart, Kolasch & Birch, LLP (57) ABSTRACT

A method and a dose planning module for planning a treatment session of a patient by means of a radiation therapy system includes a radiation therapy unit having a fixed radiation focus point. The method includes obtaining a target volume of a region of a patient to be treated during a treatment of a patient in a radiation therapy unit, the target volume being modeled as a three-dimensional voxel representation; selecting an isodose level for the planned treatment; determining shots to be delivered during the treatment, each shot being modeled by a spatial dose volume distribution of radiation represented by a three-dimensional voxel representation, the shape of the spatial distribution depending on the specific collimator setting and the selected isodose level; and selecting shots in a decreasing volume order for the dose planning.

24 Claims, 8 Drawing Sheets

EFFECTIVE VOLUME FILLING WITH TEMPLATES

FIELD OF THE INVENTION

The present invention relates to the field of radiation therapy. In particular, the invention relates to a method and a dose planning module for planning a treatment session of a patient by means of a radiation therapy system comprising a radiation therapy unit having a fixed radiation focus point.

BACKGROUND OF THE INVENTION

The development of surgical techniques has made great progress over the years. For instance, for patients requiring brain surgery, non-invasive surgery is now available which is afflicted with very little trauma to the patient.

One system for non-invasive surgery is the Leksell Gamma Knife® Perfexion system, which provides such surgery by means of gamma radiation. The radiation is emitted from a large number of fixed radioactive sources and is focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all or some radiation sources intersect or converge, causing the radiation to reach tissue-destructive levels. The point of convergence is hereinafter referred to as the "focus point".

Treatment planning optimization for radiation therapy, including for example gamma knife radio-surgery, aims at maximizing the dose delivered to the target volume within the patient (e.g. in treatment of tumours) at the same time as the dose delivered to adjacent normal tissues is minimized. In treatment planning optimization, the delivered radiation dose is limited by two competing factors where the first one is delivering a maximum dose to the target volume and the second one is delivering the minimum dose to the surrounding normal tissues.

The treatment planning optimization is a process including optimizing the number of shots being used (i.e. number of doses being delivered), the shot size, the shot time, and the position of the shot. Clearly, the irregularity and size of a target volume greatly influence the number of shots needed and the size of the shots being used to optimize the treatment. Normally, the process includes obtaining a three-dimensional representation of the target (e.g. by non-invasive image capturing by X-ray) for the radiation therapy and filling the target with spheres representing the shots without extending area strongly dosed by radiation greatly outside the target and without limited overlapping between shots). It has been shown that in order to preserve dose homogeneity (even coverage of for example an isodose level of 50%) and in a multi-shot plan, shots should not overlap with each other in a too great extent. Thus, overlapping shots may destroy the desired dose homogeneity inside the target. Further, shots protruding outside the target may result in excessive dose to surrounding normal tissues. This requires, for targets of identical volume yet different shapes, use of small shots for complicated contours (i.e. for targets having an irregular shape) and larger shots for regular shapes. In U.S. Pat. No. 6,201,988 to Bourland et al, such an optimization procedure is disclosed. Medial axis transformation (so called skeletonization) is used to characterize the target shape and to determine the shot parameters (i.e. position, collimator size and weight). According to U.S. Pat. No. 6,201,988, only skeleton points are considered for potential shot positions and the corresponding shot size is provided by the skeletonization. The shots are represented by spheres and are modeled as discs in filling process. The endpoints of the skeleton are used as start-points in the filling process. However, the treatment planning optimization shown in U.S. Pat. No. 6,201,988 may provide treatment plans having a non-optimal distribution of shot sizes, for example, an unnecessary large amount of small shot sizes may be included leading to a large number of shots being used.

Hence, there is a need of more efficient methods for planning the treatment and for optimizing the treatment planning.

SUMMARY OF THE INVENTION

An object of the present invention is to provide a more efficient method and dose planning module for planning the treatment and for optimizing the treatment planning.

A further object of the present invention is to provide a more efficient method and dose planning module for filling a target volume with shots during a treatment planning procedure.

These and other objects are fulfilled by the present invention as defined by the independent claims. Preferred embodiments are defined by the dependent claims.

The present invention is for example used in connection with treatment planning of treatment provided by means of a radiation therapy system having a collimator body provided with several groups or sets of collimator passages, each set being designed to provide a radiation beam of a respective specified cross-section toward a fixed focus. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

The term "target volume" refers to a representation of a target of a patient to be treated during radiation therapy. The target may be a tumour to be treated with radiation therapy. Typically, the representation of the target is obtained by, for example, non-invasive image capturing using X-ray or NMR.

The term "shot" refers to a delivery of radiation to a predetermined position within a target volume having a predetermined level of radiation and a spatial distribution. The shot is delivered during a predetermined period of time ("beam-on" time) via at least one sector of the collimator of the therapy system using one of the states of the sector. A "composite shot" refers to the delivery of radiation to a focus point using different collimator sizes for different sectors.

The term "beam-on time" refers to the predetermined period of time during which a shot is delivered to the target volume.

The term "overlapping" means that, in viewing the shots as 3-D volumes (defined as the volume with dose above a selected threshold, e.g. the 50% isodose level), a shot volume overlaps or intersects other shot volumes.

According to an aspect of the present invention, there is provided a method for dose planning for a radiation therapy system. The system comprises a radiation therapy unit having a fixed radiation focus point, wherein a spatial dose distribution surrounding the focus point can be changed by adjusting collimator settings. The collimator has a plurality of collimator passage inlets directing radiation emanating from radioactive sources of a source carrier arrangement of the therapy system to the focus point. The method comprises:

a) obtaining a target volume of a region of a patient to be treated during a treatment of a patient in a radiation therapy unit, the target volume being modeled as a three-dimensional voxel representation;

b) selecting an isodose level for the planned treatment;

c) determining shots to be delivered during the treatment, each shot being modelled by a spatial dose volume distribution of radiation represented by a three-dimensional voxel representation, the shape of the spatial distribution depending on the specific collimator setting and the selected isodose level;

d) selecting shots in a decreasing volume order for the dose planning comprising:

d1) initiating a position search for a specific shot to find an accepted position within the target volume;

d2) iteratively mapping different positions for the voxel representation of a current shot on the voxel representation of the target volume;

d3) checking whether predetermined conditions for each specific position are satisfied; and d4) if the predetermined conditions are satisfied for a specific position, defining that position as an accepted position and continue with step d1)-d3) for a shot having the similar shape; or d5) if the predetermined conditions are not satisfied for any position within the target volume, continuing with step d1)-d4) for a subsequent shot in the decreasing volume order.

According to a second aspect of the present invention, there is provided a dose planning unit for a radiation therapy system. The radiation therapy system comprises a radiation therapy unit having a fixed radiation focus point, wherein a spatial dose distribution surrounding the focus point can be changed by adjusting collimator settings, the collimator having a plurality of collimator passage inlets directing radiation emanating from radioactive sources of a source carrier arrangement of the therapy system to the focus point. The dose planning module comprises a template module adapted to obtain a target volume of a region of a patient to be treated during a treatment of a patient in a radiation therapy unit, the possibility to define the target volume being modeled as a three-dimensional voxel representation, and the possibility to select an isodose level for the planned treatment. Further, the template module is also adapted to provide information of shots to be used during the treatment planning, i.e. shot templates to be used in the process of filling the target with shots. Each shot is modeled by a spatial dose volume distribution of radiation represented by a three-dimensional voxel representation, the shape of the spatial distribution depending on inter alia the specific collimator setting and the selected isodose level. An operator of the radiation system or a physician planning the treatment may select a set of shots to be used during the planning. In such a case, this information will be delivered to the template module. In an alternative, the template module may use a predetermined default set of shots.

A target volume filling module is adapted to select shots in a decreasing volume order for the dose. The target volume filling module is adapted to initiate a position search for a specific shot to find an accepted position within the target volume, iteratively map different positions for the voxel representation of a current shot on the voxel representation of the target volume, check whether predetermined conditions for each specific position are satisfied, and, if the predetermined conditions are satisfied for a specific position, define that position as an accepted position and continue with a position search for a shot having the similar shape, or if the predetermined conditions are not satisfied for any position within the target volume, continue with a position search for a subsequent shot in a decreasing volume order.

In a preferred embodiment of the present invention, a target volume is filled in "shells" from the outer boundary and inwards. Voxels covered by an earlier placed shot is marked or defined as non-target. Thus, the target volume is filled in a layer-wise manner.

An optimized dose plan determined by means of the present invention, may be transferred to a radiation therapy system for use in the treatment of the patient. The dose plan determined by the invention may also or alternatively be used as input in a treatment optimization procedure where the number of shots, position of the shots and the shot sizes defined during the volume filling according to the invention serves as basis in an optimization of the number of shots, the position and the beam-on time of the respective shots and the shots sizes.

The present invention is based on the insight that an efficient and optimized treatment plan for the treatment of a target volume (e.g. a tumour) of a patient to be treated in radiation therapy can be achieved by filling a target volume representing the target volume of the patient with virtual shots representing the dose distribution for different collimator settings having sizes and volume shapes depending on the specific collimator setting and the selected isodose level. Further, the filling process (i.e. the placement of the virtual shots in the virtual target volume to successively fill the volume with shots) of the virtual shots is executed in size order. That is, the virtual volume is filled first with the virtual shots having the largest volume or size is placed according to a predetermined scheme. In order to allow that a shot is placed at a certain position, predetermined criteria or conditions must be satisfied, which will be discussed below. Hence, the virtual shots are successively mapped on the virtual target volume to find a suitable position, i.e. a position that satisfies the predetermined conditions, for a specific shot. In most practical cases, the volume cannot be filled with only shots having the largest volume or size and, therefore, the inventive procedure proceeds to the virtual shot having the second largest volume or size and successively places virtual shots having the second largest volume or size in "free spaces" in the target volume according to a predetermined scheme. The term "free spaces" refers to regions or spaces within the target volume that are not occupied by another shot and thus not are excluded from subsequent placements of shots. That is, regions or spaces in which shots have been placed are excluded in subsequent shot placements (i.e. position searches). A certain amount of overlap between adjacent shot is however allowed. The procedure is continued for shots as described above in descending size order until the target volume is filled with virtual shots.

During the filling procedure, one aim is to find a position for as many of the largest shots (measured in volume) as possible before the next level (i.e. the next level in descending volume order) of shots is selected for position finding.

Preferably, the target is filled from the outer boundary and inwards or in other words a first "shell" of shots is placed as close as possible to the outer boundary of the target before a next "shell" of shots is placed. During the filling of the second "shell", the first "shell" is excluded from the potential space of the target in which a shot can be placed.

According to an embodiment of the present invention, the check whether predetermined conditions are satisfied comprises a check whether any of the voxels of a current shot are mapped at a specific position overlaps a voxel of previously accepted positions for a shot, and, if no overlapping voxels are found, it is determined that the predetermined conditions are satisfied. Alternatively or in addition to the above overlapping restriction requirement, if overlapping voxels are found, the number of overlapping voxels is determined, and, if the number of overlapping voxels not exceeds a predetermined threshold, it is determined that the predetermined conditions are satisfied. On the other hand, if the number of overlapping voxels exceeds the predetermined threshold, it is determined that the predetermined conditions are not satisfied. The above mentioned conditions may also or alternatively include a check whether any of the voxels of the current shot is mapped on a voxel outside the outer boundary of the target volume and, if no voxel of the current volume is mapped outside the outer boundary of the target volume, determining that the predetermined conditions are satisfied. Furthermore, the conditions may alternatively or additionally include a check whether any of the voxels of the current shot is mapped on a voxel outside the outer boundary of the target volume. If at least one voxel of the current volume is mapped outside the outer boundary of the target volume, the following is performed:

determining the number of voxels mapped on voxels outside the outer boundary;

if the voxels mapped outside the outer boundary not exceeds a predetermined threshold, determining that the predetermined conditions are satisfied; or if the voxels mapped outside the outer boundary exceeds the predetermined threshold, determining that the conditions are not satisfied.

Alternatively or in addition to the above, the conditions may include a check whether any of the voxels of the current shot is mapped on a voxel outside the outer boundary of the target volume. If at least one voxel of the current volume is mapped outside the outer boundary of the target volume, the following is performed:

determining the maximum voxel length that any part of the shot is extending outside the outer boundary; and if this maximum voxel length exceeds a predetermined maximal length, determining that the conditions are not satisfied.

Alternatively or in addition to the above, the conditions may include a check whether any of the voxels of the current shot is mapped on a voxel outside the outer boundary of the target volume. If no voxel of the current volume is mapped outside the outer boundary of the target volume, the following is performed:

determining the minimum voxel length from the outer boundary to any part of the shot; and if this minimum voxel length exceeds a predetermined maximal length, determining that the conditions are not satisfied.

These conditions may be combined in different set ups or all conditions may be used. They may be ranked or checked according to different orders. For example, they can be ranked and thus checked in accordance with required computational power.

In order to obtain an even more complete and space efficient filling of the target volume, different starting positions and search orders are selected for each new procedure for placing a specific shot within the target. Thus, initiating a position search for a specific shot to find an accepted position within the target volume comprises initiating a position search for an accepted position of a specific shot at a predetermined starting point in the target volume. The predetermined starting point and search order will change from one position search to a subsequent position search in accordance with a predetermined scheme. Preferably, different corners of the target volume are selected as starting points.

Preferably, defining a position as an accepted position for a specific shot comprises excluding the volume of the target volume corresponding to the volume of the specific shot at the accepted position in a subsequent position search for an accepted position of a specific shot.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

DETAILED DESCRIPTION OF THE DRAWINGS

Figure 1:
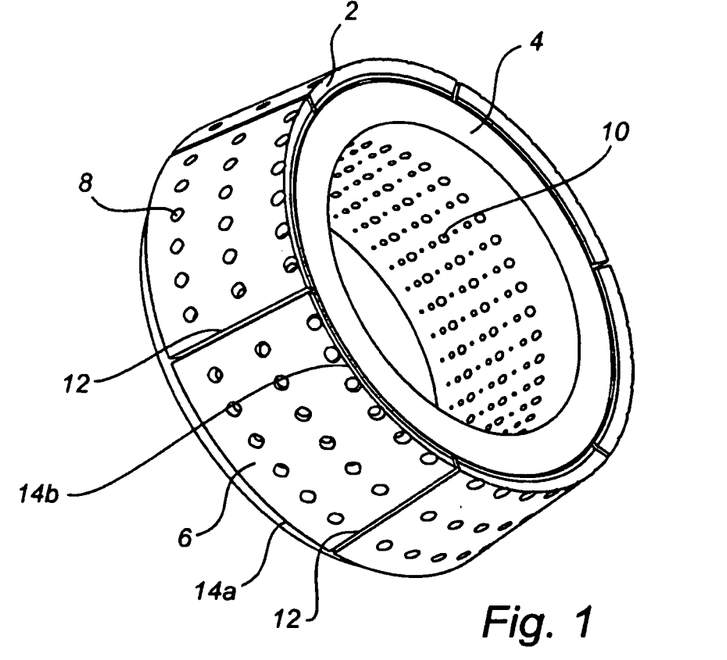
FIG. 1 is a perspective view of an assembly comprising a source carrier arrangement surrounding a collimator body, in accordance with an embodiment of the invention.

With reference to FIGS. 1-5, an exemplary radiation therapy device in which a treatment plan developed using the present invention can be used for treatment of a patient. FIG. 1 is a perspective view of an assembly comprising a source carrier arrangement 2 surrounding a collimator body 4. The source carrier arrangement 2 and the collimator body 4 both have the shape of a frustum of a cone. The source carrier arrangement 2 comprises six segments 6 distributed along the annular circumference of the collimator body 4. Each segment 6 has a plurality of apertures 8 into which containers containing radioactive sources, such as cobalt, are placed. The collimator body 4 is provided with collimator passages or channels, internal mouths 10 of the channels are shown in the figure.

Each segment 6 has two straight sides 12 and two curved sides 14a, 14b. One of the curved sides 14a forms a longer arc of a circle, and is located near the base of the cone, while the other curved side 14b forms a shorter arc of a circle. The segments 6 are linearly displaceable, that is they are not rotated around the collimator body 4, but are instead movable back and forth along an imaginary line drawn from the center of the shorter curved side 14b to the center of the longer curved side 14a. Such a translation displacement has the effect of a transformation of coordinates in which the new axes are parallel to the old ones.

As can be seen from FIG. 1 there is a larger number of internal mouths 10 or holes of the collimator passages than the number of apertures 8 for receiving radioactive sources. In this particular case there are three times as many collimator passages as there are apertures for receiving radioactive sources, such as e.g. 180 apertures and 540 collimator passages. The reason for this is that there are three different sizes of collimator passages in the collimator body 4, or rather passages which direct radiation beams with three different diameters, toward the focus. The diameters may e.g. be 4, 8 and 16 mm. The three different types of collimator passages are each arranged in a pattern which corresponds to the pattern of the apertures in the source carrier arrangement. The desired size or type of collimator passage is selected by displacing the segments 6 of the source carrier arrangement linearly along the collimator body so as to be in register with the desired collimator passages.

Figure 2:
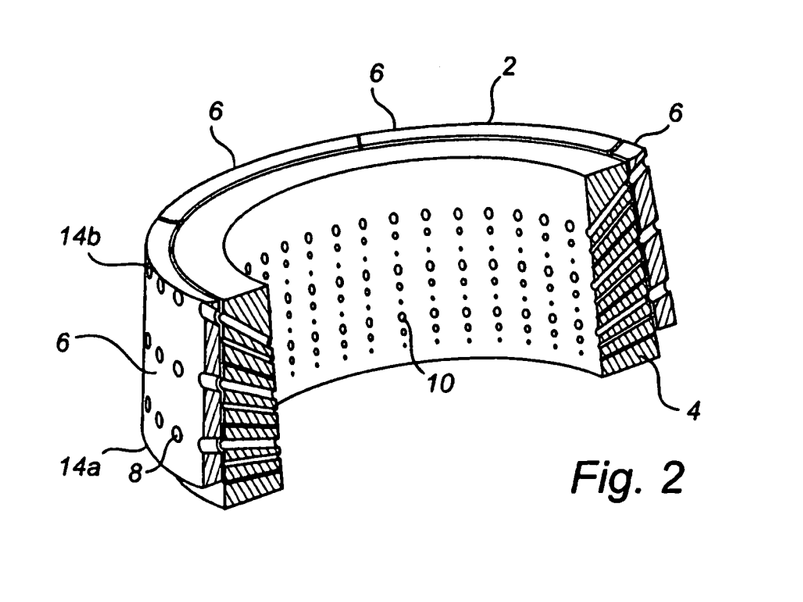
FIG. 2 is sectional view in perspective of the assembly shown in FIG. 1.

FIG. 2 is sectional view in perspective of the assembly shown in FIG. 1. The same reference numerals are used for details which are the same as in FIG. 1. This also applies to the following FIGS. 3 and 4.

Figure 3:
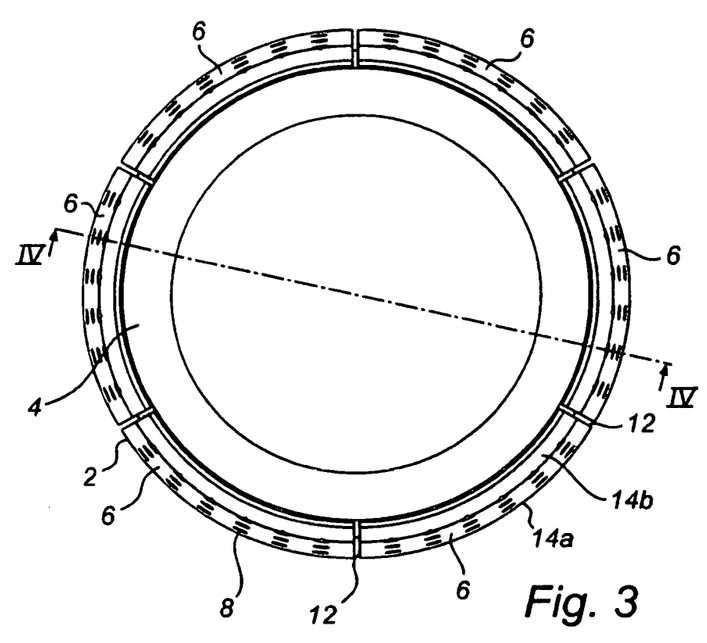
FIG. 3 is a view from the backside of the assembly shown in FIG. 1.

FIG. 3 is a view from the backside of the assembly shown in FIG. 1. This is the side with smaller diameter, while the other side, having a larger diameter, is the front or patient side, i.e. where the patient's body is introduced.

Figure 4:
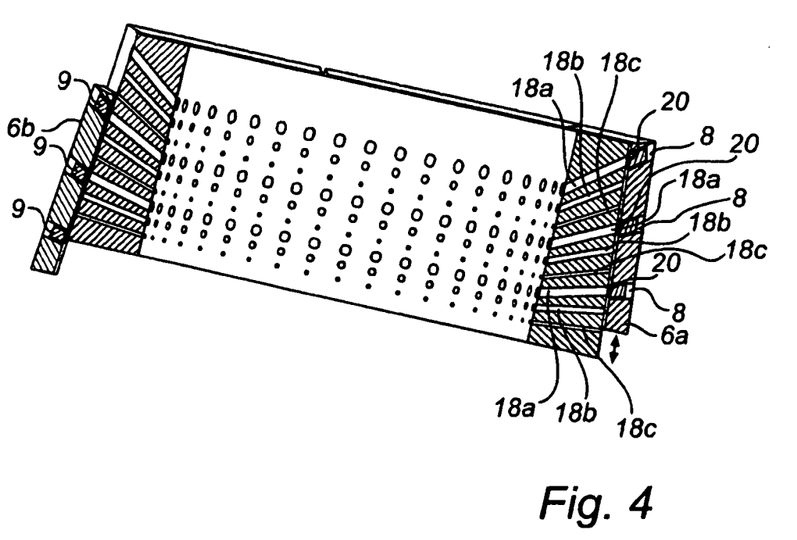
FIG. 4 is a view in cross-section along line IV-IV in FIG. 3.

FIG. 4 is a view in cross-section along line IV-IV in FIG. 3. Thus, in FIG. 4 two segments 6a and 6b are shown. Starting with one of the segments 6a, in this view it can be seen that there are nine collimator passages 18a-18c available for three radioactive sources 9 contained in a respective aperture 8 in the source carrier arrangement. The sizes of the collimators 18a-18c are arranged in an alternating sequence, such as for instance, the first collimator passage 18a providing a beam of 16 mm in diameter, the second collimator passage 18b providing a beam of 8 mm in diameter, the third collimator passage 18c providing a beam of 4 mm in diameter, the fourth collimator passage 18a starting the sequence all over by providing a beam of 16 mm in diameter, etc. However, the collimator passages 18a-18c could, alternatively, be arranged in another order, e.g. to provide the sequence 16 mm, 4 mm, 8 mm. In the figure the apertures 8 of the source carrier arrangement are arranged in register with the first, fourth and seventh collimator passages 18a, or rather their respective inlets, the collimator passages all providing a beam of 16 mm in diameter at the focus. Each segment may be individually displaced in a straight direction as is illustrated with the double-headed arrow in order to select another group of collimator passages, i.e. another beam diameter size for any segment. If the segment is displaced so that the radioactive sources 9 face a surface in between the collimator passages, those radioactive sources will be shut off, i.e. essentially no or only a minimum radiation from those sources will reach the focus. A segment may also like the segment 6b in FIG. 4 be displaced to such an extent that one of the three shown apertures will be located beside and outside of the first or ninth collimator passage. This allows of the possibility to arrange only two of the three radiation sources 9 in register with two collimator passages. Thus, this and other embodiments do not only enable that differently sized beams are simultaneously directed from different directions toward a common focus, but also that different numbers of beams may simultaneously be directed from different directions.

As can be seen in FIG. 4 the nine collimator passages 18a-18c are arranged at somewhat different angles in order for the beams to be directed to the common focus, regardless of which collimator passage or passages that are used at the moment. The angle of extension direction of the first to the last collimator passage having the same cross-section is, in this case, at least 30°.

Figure 5:
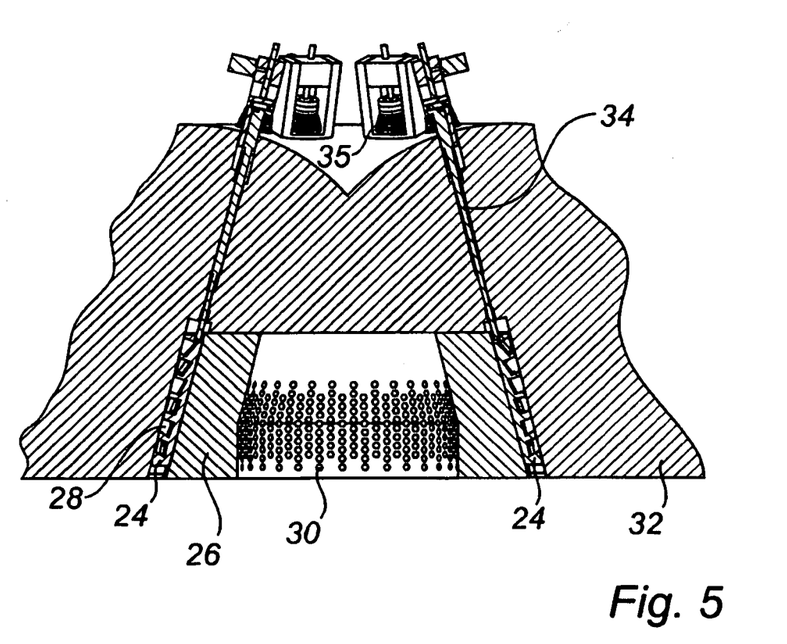
FIG. 5 is a sectional view of an assembly of the type shown in FIGS. 1-4, the assembly being illustrated with an actuating mechanism and a rear radiation protection structure.

FIG. 5 is a sectional view of an assembly of the type shown in FIGS. 1-4, the assembly being illustrated with an actuating mechanism and a rear radiation protection structure. Accordingly, a source carrier arrangement having a plurality of segments 24 is provided. Each segment 24 has a number of apertures 28 in which sources are inserted. The segments 24 are arranged around a collimator body 26 having collimator passages (not shown) with mouths 30 directing radiation beams towards a focus.

The segments are surrounded by a rear radiation protection structure 32, so as to minimize or eliminate leakage of radiation to the nursing personnel. The rear protection structure 32 is dimensioned and made of a suitable material, such as casting material, accordingly. A front radiation protection structure (not shown) is suitably also provided, preferably of smaller dimension so as to facilitate access to the treatment space, but with a high density material, such as lead, tungsten or depleted uranium.

An actuating mechanism is provided for displacing the segments in a linear direction of motion. The maximum displacement distance for a segment may e.g. be 60 mm, however larger or smaller distances are also conceivable. The actuating mechanism comprises a number of supporting rods or arms 34, each arm being connected to a respective segment 24. The arms 34 extend through a respective bore in the rear radiation protection structure 32 and are movable along their direction of elongation. The arm and the bore are designed so as to form a labyrinth passage having different portions of overlapping diameters, thereby minimizing or eliminating the escape of hazardous radiation through the bore. Each arm is individually controlled by means of a respective rotational electrical motor. The electrical motor has a high resolution with a positioning encoder and a ball roller screw enabling a precise linear positioning of the arm 34 and the segment 24. A spring means 35 is arranged to affect the arms and ensure that they displace the segments so that the radioactive sources will be in a complete shut-off position in case of power failure. The arms 34 may be disconnected from the segments 24, when the segments are to be provided with new radioactive sources. In such case the loading is suitably done through channels (not shown) provided in one area of in the rear radiation protection structure 32. The loading procedure may be performed in a conventional manner as in the prior art, e.g. a procedure corresponding to the one used in connection with Leksell Gamma Knife® Perfexion. However, alternative procedures are also conceivable.

Figures 6A, 6B, 6C:
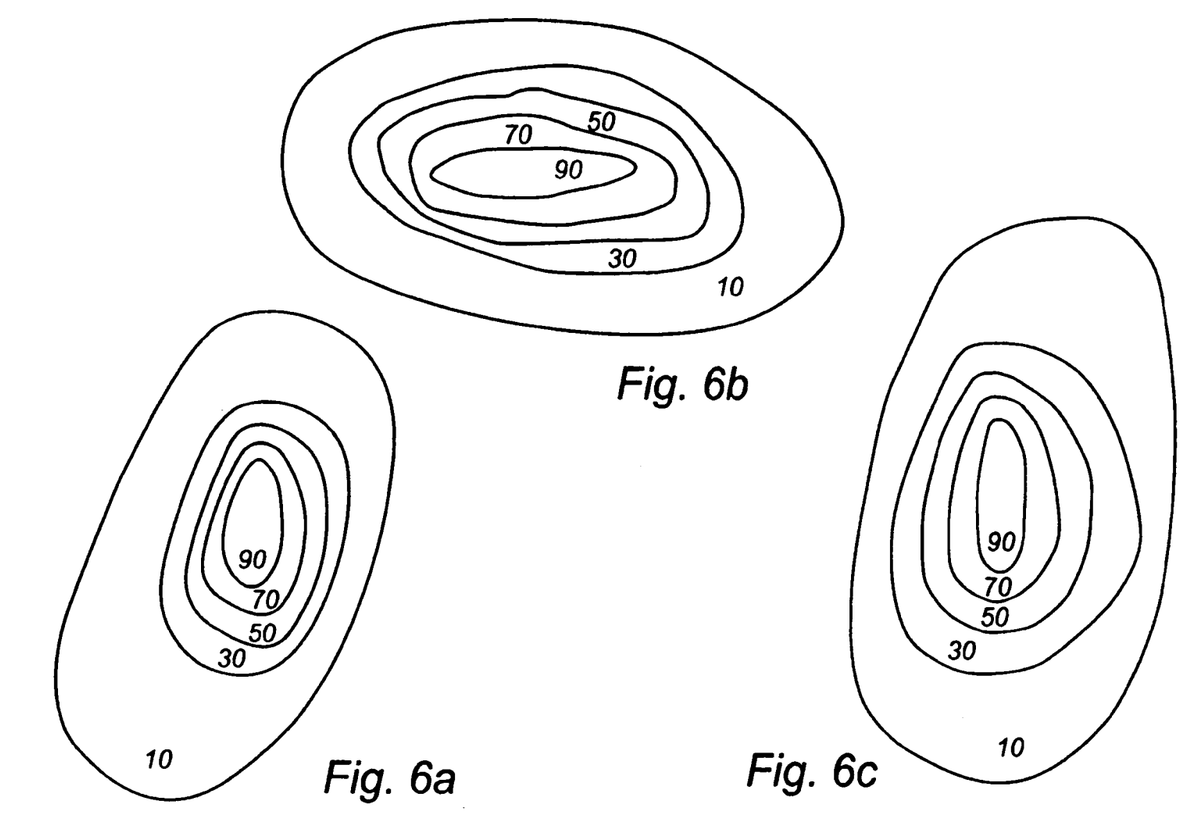
FIGS. 6a-6c show schematic representations of the dose distribution in three central planes of a composite shot.

In FIG. 6a-c, the dose distributions along three central planes for a single composite shot (i.e. using different collimator sizes in different sectors) are schematically shown. The high dose levels are confined to small regions and the surrounding region exhibits a limited dose. In general, for a larger or irregular target shape, multiple shots have to be used cover different parts of the target region.

Figure 7A:
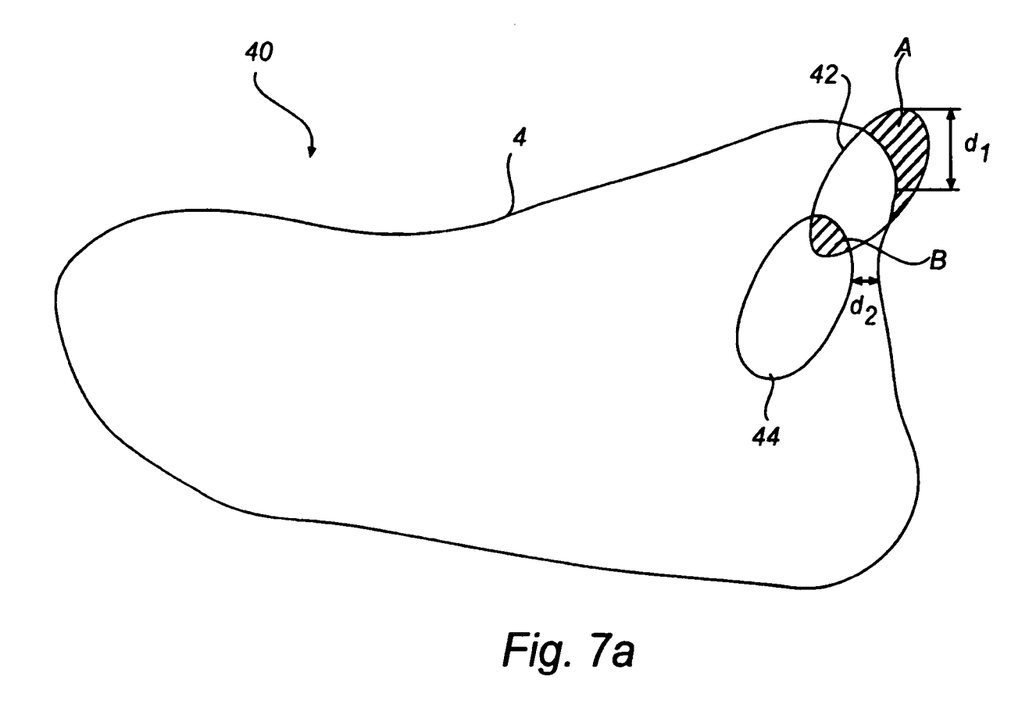
FIG. 7a is a schematic illustration of shots placed within a target.
Figure 7B:
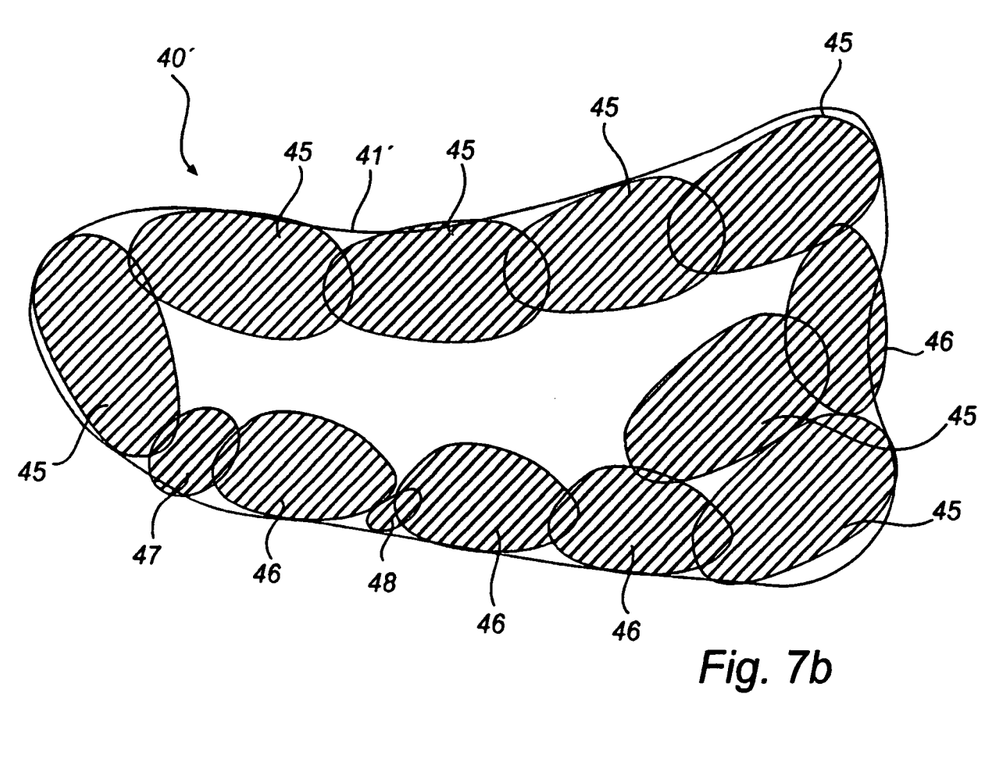
FIG. 7b is a schematic illustration of shots placed within a target.
Figure 8:
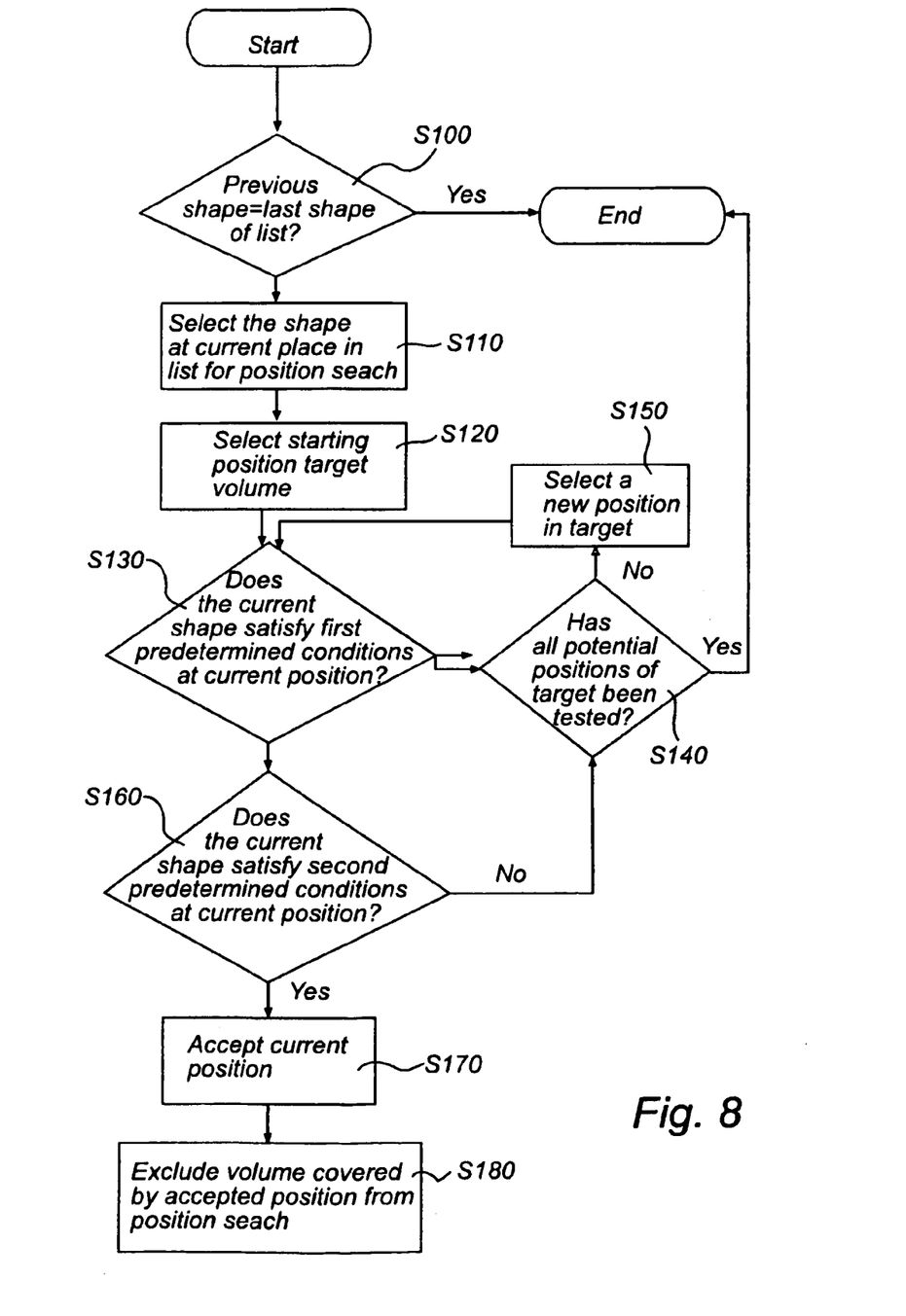
FIG. 8 is a flow diagram illustrating the steps of an embodiment of the method according to the present invention.

With reference now to FIG. 8, a preferred embodiment of the method according to the present invention will be discussed. The algorithm according to the method uses shapes to model the shots, where the size and shape of the isosurface depends inter alia on the isodose level and selected sector and collimator configuration. Hence, the shapes are defined by isosurfaces of the shots calculated for the planning isodose level. According to the method, the shots are sorted in a list based on the size of volume encapsulated by its isodose surface. The target volume, defined by a binary three-dimensional image (i.e. a voxel space), is searched for voxels where a current shot touches, or almost touches, the outer boundary surface of the target, without extending too much outside the target volume and without overlapping too much with previously placed shots. This will now be described and illustrated in more detail below with reference to FIGS. 7a, 7b and 8.

At step S100, it is checked whether the end of list has been reached, i.e. whether a position search has been performed for all shots. The shots (i.e. the three-dimensional representations of the shots) are ordered in decreasing size or volume order, which means that the algorithm first will try to find an accepted position for the largest shot. Normally, the list will contain about 3-20 different shots in different sizes. In fact, the algorithm will search the target volume for accepted positions for shots of the largest size until no such accepted position can be found. When no further accepted position can be found for a shot of the largest size or shape, the algorithm proceeds to a shot of the second largest size or shape and so on until all shots of the list has been tested. If all shots have been tested and no further accepted positions can be found, the procedure is ended.

Thereafter, at step S110, a shot for a position search is selected from the list in accordance with the above. At step S120, a starting position for the position search for the current shot is selected. According to embodiments, the starting positions may be selected such that a first corner of the target volume grid selected for a first position search, a second corner for a second position search, a third corner for a third position search etc.

At step S130, it is checked whether the current shot positioned at a current position satisfies first predetermined conditions. In FIGS. 7a and 7b, it is illustrated schematically how shots can be placed in a target volume 40, 40'.

In one embodiment of the present invention, the first predetermined conditions may include a check whether the current shot is placed adjacent to the surface (i.e. an outer boundary) of the target (i.e. whether at least one voxel of the current shot is adjacent to at least one voxel of the outer boundary of the target volume) or extending outside the outer boundary. It is also checked whether the current shot extends too much outside the outer boundary of the target volume. Preferably, the current volume is allowed to extend a predetermined number of voxels outside the target volume. With reference to FIG. 7a, the area A extends outside the outer boundary 41 of the target volume 40 and it is thus checked whether area A is too large, i.e. whether the voxels of area A exceeds a predetermined number.

If the above mentioned conditions are not satisfied, the algorithm proceeds to step S140 and S150 where it is checked whether all potential positions within the target volume has been tested, i.e. whether there remains non-excluded volume within the target, and if not, a new potential position within the target is selected and the algorithm returns to step S130. Alternatively, the algorithm may select the next non-excluded position and return to step S130 for a new test as long as there is any non-excluded volume that not has been tested during the position search for the current shot. Thereafter, the algorithm may end the procedure. In addition to the conditions discussed above, there are further conditions that may be checked. For example, it may be checked whether any of the voxels of the current shot is mapped on a voxel outside the outer boundary of the target volume. If at least one voxel of the current volume is mapped outside the outer boundary of the target volume, the following may be performed: determining a voxel length of a part of the shot extending outside the outer boundary, and, if the extending voxel length exceeds a predetermined maximal length, determining that the conditions are not satisfied. With reference to FIG. 7a, it may be checked whether the distance $d_1$ extends too long outside the outer boundary 41.

Another condition that can be used alternatively to the first requirement discussed above where at least one shot voxel must touch or extend outside the target volume, is to determine a minimum voxel length from any voxel of the shot to the outer boundary 41 and if this voxel length is larger than a predetermined maximum length, it is determined that the conditions are not satisfied. In FIG. 7a, this illustrated with the distance $d_2$.

The conditions discussed above (i.e. the requirement of a maximum number of overlapping voxels, the requirement of a minimum number of voxels outside the outer boundary of the target volume, the maximum length of an extending part of the shot, and the minimum length from any voxel of the shot to the outer boundary of the target volume) can be ranked or can be given different "importance weights" based on different criteria, for example, the computational power they require.

If the first predetermined conditions are found to be satisfied, the algorithm proceeds to step S160 where it is checked whether the current shot positioned at the current position satisfies second predetermined conditions. In one embodiment, this step includes a check whether the current shot overlaps previously accepted positions for a shot (i.e. excluded regions). Preferably, a current shot is allowed to overlap a previously accepted position for a shot with a predetermined number of voxels. In FIG. 7a, the current shot 42 overlaps a previously placed shot 44 with the area B and it is hence checked whether this area B is too large, i.e. consists of too many voxels.

If this second predetermined conditions are not satisfied, the algorithm returns to steps S140 and S150. However, if the second predetermined conditions are satisfied, the algorithm proceeds to step S170 where the current position is accepted as an allowed or accepted position for the current shot. At step S180, the accepted position for the current shot (i.e. the accepted volume) is excluded from the target volume in further positioned searches. In FIG. 7a, the space occupied by the previously positioned shot 44 is excluded from subsequent positioned searches. After having excluded the positioned shot in step S180, the algorithm returns to step S100.

It should be noted that the predetermined conditions may have a different order when checked for a specific shot. For example, the check whether a current shot overlaps a previously placed shot (i.e. excluded volume or space) with a too large area may be performed first.

With reference now to FIG. 7b, the "shell-wise" or "layer-wise" filling of the target volume will be discussed. The target volume 40' has been filled with a first shell of shots 45, 46, 47, and 48, indicated with vertical lines. The space occupied or covered by these shots is excluded from the volume filling when the second shell of shots is to be placed within the target 40'. In this illustrated example, a first shot 45 indicated with horizontal lines is placed in the second shell of shots. Hence, as can be seen, the target volume 40' is filled from the outer boundary 41' and inwards, which provides for an efficient filling of the target volume 40'. When all shots in a template has been tested for placement within the target 40', the voxels covered with a shot are marked as "non-target". Thereafter, the free area of the target (i.e. the area not covered by previously placed shots) is now the area within the target 40' in which shots can be placed in the next loop of shot placement. That is, the procedure starts again with placing the shots of the template in order. This is continued inwards until no more shots can be placed within the target.

Figure 9:
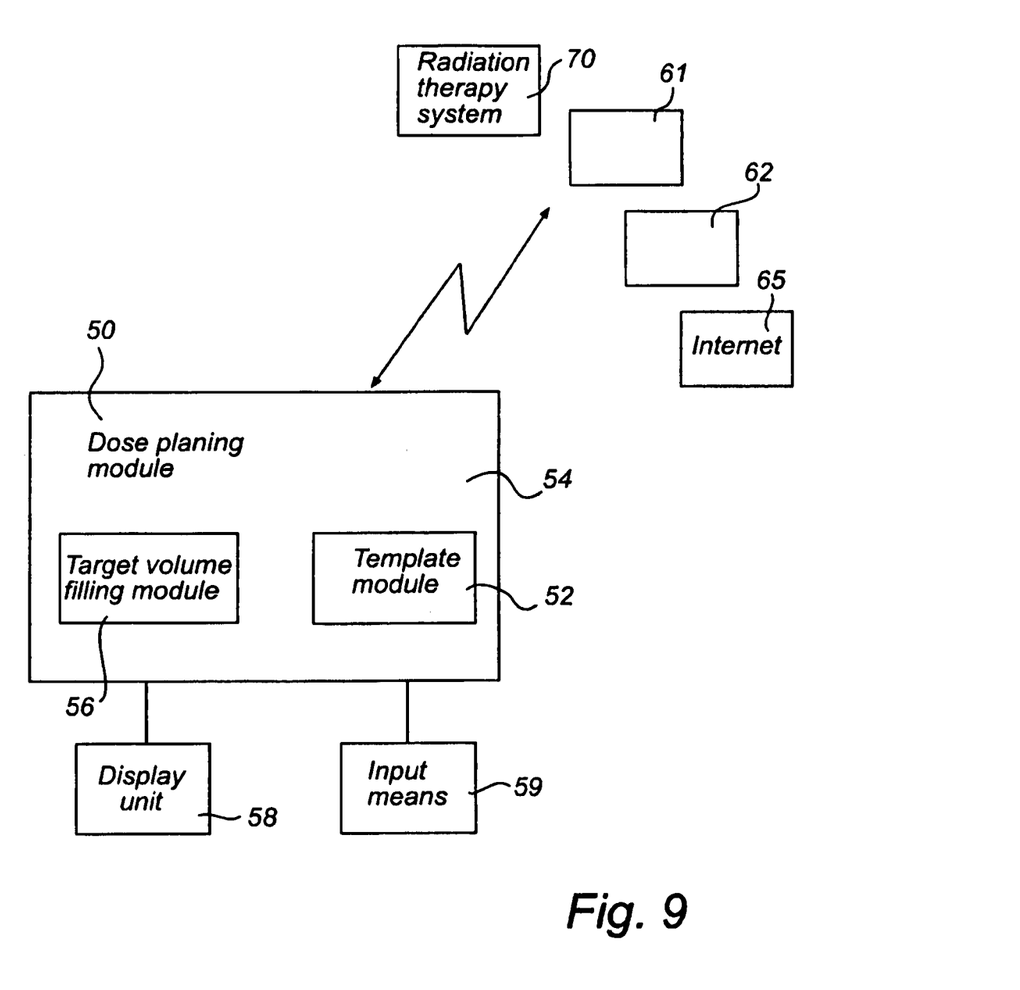
FIG. 9 shows an embodiment of a dose planning module according to the present invention.

Turning now to FIG. 9, an embodiment of a dose planning module according to the present invention will be discussed. A dose planning module 50 according to the present invention may, for example, be integrated in computer device such as a computerized system, a personal computer etc. provided with a display unit. The dose planning module 50 may be connected to other devices 61, 62 such as other personal computer, servers, medical systems etc at a hospital or care provider institution via a network 60, e.g. wirelessly by means of Bluetooth or via a cable network. Further, the dose planning module 50 may be connected to other networks such as the Internet 65 wirelessly by means of Bluetooth or via a cable network. An optimized dose plan determined by means of the dose planning module 50 may be transferred to a radiation therapy system 70, for example, the radiation therapy system described above with reference to FIG. 1-5. For example, the optimized dose plan may be transferred wirelessly via the network 60 to the radiation therapy system 70. The dose plan determined by the invention may also or alternatively be used as input in a treatment optimization procedure where the number of shots, position of the shots and the shot sizes defined during the volume filling according to the invention serves as basis in an optimization of the number of shots, the position of the respective shots and the shots sizes.

Furthermore, information or data, for example, about a specific patient to be treated by radiation therapy can be obtained via the network 60 from other device or system 61, 62. For example, a three-dimensional representation of the target (e.g. by non-invasive image captured by X-ray) for the radiation therapy can be obtained from the X-ray system.

In an embodiment of the dose planning module 50 a template module 52 is adapted to obtain a target volume of a region of a patient to be treated during a treatment of a patient in a radiation therapy unit, which target volume is modeled as a three-dimensional voxel representation. The template module 52 is further adapted to obtain an isodose level for the planned treatment. The isodose level may, for example, be input an operator or physician optimizing the dose plan manually via a display unit 58 and input means 59 such as a keyboard and/or a mouse connected to the dose planning module or of a personal computer in which the dose planning module 50 is integrated. Further, the template module 52 is adapted to obtain information of shots to be used, i.e. to select which shot templates to use in the position searches, in a dose planning and to be delivered during a treatment. Each shot is modeled by a spatial dose volume distribution of radiation represented by a three-dimensional voxel representation and shape of the spatial distribution depends on the specific collimator setting and the selected isodose level. The shot templates to be used can be input manually by the operator or physician or can be obtained from a register or memory, for example, of the dose planning module 50 containing predetermined templates of shot combinations.

A target volume filling module 56 is adapted to fill the virtual target volume representing the target volume with virtual shots representing the dose distribution for different collimator settings having sizes and volume shapes depending on the specific collimator settings. Further, the filling process (i.e. the placement of the virtual shots in the virtual target volume to successively fill the volume with shots) of the virtual shots is executed in size order. The method or algorithm for obtaining this has been described above with reference to FIG. 6. In particular, the target volume filling module 56 is adapted to select shots in a decreasing volume order for the dose and to initiate a position search for a specific shot to find an accepted position within the target volume. Further, different positions for the voxel representation of a current shot are iteratively mapped on the voxel representation of the target volume and it is checked whether predetermined conditions for each specific position are satisfied. If the predetermined conditions are satisfied for a specific position, that position is defined as an accepted position and continue with a position search for a shot having the similar shape, or if the predetermined conditions are not satisfied for any position within the target volume, position search for a subsequent shot in a decreasing volume order is initiated.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting.

The invention claimed is:

1. A method for dose planning for a radiation therapy system, the radiation therapy system comprising a radiation therapy unit having a fixed radiation focus point, wherein a spatial dose distribution surrounding the focus point can be changed by adjusting collimator settings, said collimator having a plurality of collimator passage inlets directing radiation emanating from radioactive sources of a source carrier arrangement of the therapy system to said focus point, said method comprising:
   a) obtaining a target volume of a region of a patient to be treated during a treatment of a patient in a radiation therapy unit, said target volume being modeled as a three-dimensional voxel representation;
   b) selecting an isodose level for a planned treatment;
   c) determining shots to be delivered during said treatment, each shot being modelled by a spatial dose volume distribution of radiation represented by a three-dimensional voxel representation, the shape of said spatial distribution depending on a specific collimator setting and said selected isodose level;
   d) selecting a first layer of shots in a decreasing volume order for filling a first space immediately adjacent to an outer boundary of the target volume represented by the three-dimensional voxel representation, the first space extending along the entire outer boundary of the target volume, comprising the sub-steps of:
      d1) initiating a position search for a specific shot to find an accepted position within the first space of said target volume;
      d2) iteratively mapping different positions for the voxel representation of a current shot in the first space of the voxel representation of the target volume; and
      d3) checking whether predetermined conditions for each specific position are satisfied, comprising the sub-steps of:
         d3i) if the predetermined conditions are satisfied for a specific position, defining that position as an accepted position and continuing with steps d1)-d3) for a shot having a similar shape; and
         d3ii) if the predetermined conditions are not satisfied for any position within the target volume, continuing with steps d1)-d3) for a subsequent shot in said decreasing volume order;
   e) selecting a second layer of shots in a decreasing volume order for filling a second space immediately adjacent to the first space in a radially inward direction, an outer boundary of the second space being defined by an inner boundary of the first layer of shots, comprising the sub-steps of:

e1) initiating a position search for a specific shot to find an accepted position within the second space of said target volume;

e2) iteratively mapping different positions for the voxel representation of a current shot in the second space of the voxel representation of the target volume; and e3) checking whether predetermined conditions for each specific position are satisfied, comprising the sub-steps of:

e3i) if the predetermined conditions are satisfied for a specific position, defining that position as an accepted position and continuing with steps e1)-e3) for a shot having a similar shape; or e3ii) if the predetermined conditions are not satisfied for any position within the target volume, continuing with steps e1)-e3) for a subsequent shot in said decreasing volume order, wherein the step e) of selecting the second layer of shots is performed after no more shots can be placed within the first space through the sub-steps of d1)-d3).

2. The method according to claim 1, wherein the step of checking whether predetermined conditions are satisfied comprises:

checking whether any voxel of a current shot is mapped at a specific position overlapping a voxel of previously accepted positions for a shot; and if no overlapping voxels are found, determining that the predetermined conditions are satisfied.

3. The method according to claim 2, wherein the step of checking whether predetermined conditions are satisfied comprises:

checking whether any voxel of a current shot is mapped at a specific position overlapping a voxel of previously accepted positions for a shot;

if overlapping voxels are found, performing the following:

determining a number of overlapping voxels; and if the number of overlapping voxels does not exceed a predetermined threshold, determining that the predetermined conditions are satisfied; or if the number of overlapping voxels exceeds said predetermined threshold, determining that the predetermined conditions are not satisfied.

4. The method according to claim 1, wherein the step of checking whether predetermined conditions are satisfied comprises:

checking whether any voxel of a current shot is mapped at a specific position overlapping a voxel of previously accepted positions for a shot;

if overlapping voxels are found, performing the following:

determining a number of overlapping voxels; and if the number of overlapping voxels does not exceed a predetermined threshold, determining that the predetermined conditions are satisfied; or if the number of overlapping voxels exceeds said predetermined threshold, determining that the predetermined conditions are not satisfied.

5. The method according to claim 1, wherein the step of checking whether predetermined conditions are satisfied comprises:

checking whether any voxel of the current shot is mapped on a voxel outside an outer boundary of said target volume; and if no voxel of a current volume is mapped outside said outer boundary of said target volume, determining that said predetermined conditions are satisfied.

6. The method according to claim 5, wherein the step of checking whether predetermined conditions are satisfied comprises:

checking whether any voxel of the current shot is mapped on a voxel outside said outer boundary of said target volume;

if at least one voxel of said current volume is mapped outside said outer boundary of said target volume, performing the following:

determining a maximum voxel length that any part of the shot is extending outside the outer boundary; and if said maximum voxel length exceeds a predetermined maximal length, determining that said conditions are not satisfied.

7. The method according to claim 1, wherein the step of checking whether predetermined conditions are satisfied comprises:

checking whether any voxel of the current shot is mapped on a voxel outside said outer boundary of said target volume;

if at least one voxel of a current volume is mapped outside an outer boundary of said target volume, performing the following:

determining a number of voxels mapped on voxels outside said outer boundary;

if said voxels mapped outside said outer boundary does not exceed a predetermined threshold, determining that said predetermined conditions are satisfied; or if said voxels mapped outside said outer boundary exceeds said predetermined threshold, determining that said conditions are not satisfied.

8. The method according to claim 7, wherein the step f checking whether predetermined conditions are satisfied comprises:

checking whether any voxel of the current shot is mapped on a voxel outside said outer boundary of said target volume;

if at least one voxel of said current volume is mapped outside said outer boundary of said target volume, performing the following:

determining a maximum voxel length that any part of the shot is extending outside the outer boundary; and if said maximum voxel length exceeds a predetermined maximal length, determining that said conditions are not satisfied.

9. The method according to claim 1, wherein the step of checking whether predetermined conditions are satisfied comprises:

if no voxel of a current volume is mapped outside an outer boundary of the target volume, the following is performed:

determining a minimum voxel length from the outer boundary to any part of the shot; and if this minimum voxel length exceeds a predetermined maximal length, determining that the conditions are not satisfied.

10. The method according to claim 1, wherein initiating a position search for a specific shot to find an accepted position within said target volume comprises initiating a position search for an accepted position of a specific shot at a predetermined starting point in said target volume, wherein said predetermined starting point and search order will change from a position search to a subsequent position search in accordance with a predetermined scheme.

11. The method according to claim 1, wherein defining a position as an accepted position for a specific shot comprises excluding a volume of the target volume corresponding to a volume of the specific shot at the accepted position in a subsequent position search for an accepted position of a specific shot.

12. The method according to claim 1, wherein during selecting the first layer of shots, each of the selected shots, except for a first shot, has a volume no greater than a volume of a previously selected shot.

13. A dose planning unit for a radiation therapy system, the radiation therapy system comprising a radiation therapy unit having a fixed radiation focus point, wherein a spatial dose distribution surrounding the focus point can be changed by adjusting collimator settings, said collimator having a plurality of collimator passage inlets directing radiation emanating from radioactive sources of a source carrier arrangement of the therapy system to said focus point, said dose planning unit comprising:

a template module adapted to:
obtain a target volume of a region of a patient to be treated during a treatment of a patient in a radiation therapy unit, said target volume being modeled as a three-dimensional voxel representation;
obtain an isodose level for a planned treatment; and
provide information of shots to be delivered during said treatment, each shot being modelled by a spatial dose volume distribution of radiation represented by a three-dimensional voxel representation, the shape of said spatial distribution depending on a specific collimator setting and said selected isodose level; and a target volume filling module adapted to
select a first layer of shots in a decreasing volume order for filling a first space immediately adjacent to an outer boundary of the target volume represented by the three-dimensional voxel representation, the first space extending along the entire outer boundary of the target volume; and
select a second layer of shots in a decreasing volume order for filling a second space immediately adjacent to the first space in a radially inward direction, an outer boundary of the second space being defined by an inner boundary of the first layer of shots, said target volume filling module being adapted to:
initiate a position search for a specific shot to find an accepted position within said target volume;
iteratively map different positions for the voxel representation of a current shot on the voxel representation of the target volume;
check whether predetermined conditions for each specific position are satisfied; and
if the predetermined conditions are satisfied for a specific position, define that position as an accepted position and continue with a position search for a shot having a similar shape; or
if the predetermined conditions are not satisfied for any position within the target volume, continue with a position search for a subsequent shot in a decreasing volume order,
wherein the target volume filling module is configured to select the second layer of shots for filling the second space after no more shots can be placed within the first space.

14. The dose planning unit according to claim 13, wherein said target volume filling module is adapted to:
check whether any voxel of a current shot is mapped at a specific position overlapping a voxel of previously accepted positions for a shot; and
if no overlapping voxels are found, determine that the predetermined conditions are satisfied.

15. The dose planning unit according to claim 14, wherein said target volume filling module is adapted to:
check whether any voxel of a current shot is mapped at a specific position overlapping a voxel of previously accepted positions for a shot;
if overlapping voxels are found, perform the following:
determining a number of overlapping voxels; and
if the number of overlapping voxels does not exceed a predetermined threshold, determine that the predetermined conditions are satisfied; or
if the number of overlapping voxels exceeds said predetermined threshold, determine that the predetermined conditions are not satisfied.

16. The dose planning unit according to claim 13, wherein said target volume filling module is adapted to:
check whether any voxels of a current shot is mapped at a specific position overlapping a voxel of previously accepted positions for a shot;
if overlapping voxels are found, perform the following:
determining a number of overlapping voxels; and
if the number of overlapping voxels does not exceed a predetermined threshold, determine that the predetermined conditions are satisfied; or
if the number of overlapping voxels exceeds said predetermined threshold, determine that the predetermined conditions are not satisfied.

17. The dose planning unit according to claim 13, wherein said target volume filling module is adapted to:
check whether any voxel of the current shot is mapped on a voxel outside an outer boundary of said target volume; and
if no voxel of a current volume is mapped outside said outer boundary of said target volume, determine that said predetermined conditions are satisfied.

18. The dose planning unit according to claim 17, wherein said target volume filling module is adapted to:
check whether any voxel of the current shot is mapped on a voxel outside said outer boundary of said target volume;
if at least one voxel of said current volume is mapped outside said outer boundary of said target volume, perform the following:
determining a maximum voxel length that any part of the shot is extending outside said outer boundary; and
if said maximum voxel length exceeds a predetermined maximal length, determining that said conditions are not satisfied.

19. The dose planning unit according to claim 13, wherein said target volume filling module is adapted to:
check whether any voxel of the current shot is mapped on a voxel outside an outer boundary of said target volume;
if at least one voxel of a current volume is mapped outside said outer boundary of said target volume, perform the following:
determining a number of voxels mapped on voxels outside said outer boundary;
if said voxels mapped outside said outer boundary does not exceed a predetermined threshold, determine that said predetermined conditions are satisfied; or
if said voxels mapped outside said outer boundary exceeds said predetermined threshold, determine that said conditions are not satisfied.

20. The dose planning unit according to claim 19, wherein said target volume filling module is adapted to:
check whether any voxel of the current shot is mapped on a voxel outside said outer boundary of said target volume;

if at least one voxel of said current volume is mapped outside said outer boundary of said target volume, perform the following:
    determining a maximum voxel length that any part of the shot is extending outside said outer boundary; and
    if said maximum voxel length exceeds a predetermined maximal length, determining that said conditions are not satisfied.

21. The dose planning unit according to claim 13, wherein said target volume filling module is adapted to:
If no voxel of a current volume is mapped outside an outer boundary of the target volume, perform the following:
    determining a minimum voxel length from the outer boundary to any part of the shot; and
    if this minimum voxel length exceeds a predetermined maximal length, determine that the conditions are not satisfied.

22. The dose planning unit according to claim 13, wherein said target volume filling module is adapted to initiate a position search for a specific shot to find an accepted position within said target volume by initiating a position search for an accepted position of a specific shot at a predetermined starting point and search order in said target volume, wherein said predetermined starting point and search order will change from a position search to a subsequent position search in accordance with a predetermined scheme.

23. The dose planning unit according to claim 13, wherein defining a position as an accepted position for a specific shot comprises excluding a volume of the target volume corresponding to a volume of the specific shot at the accepted position in a subsequent position search for an accepted position of a specific shot.

24. The dose planning unit according to claim 13, wherein the target volume filling module is configured in such a manner that during selecting the first layer of shots, each of the selected shots, except for a first shot, has a volume no greater than a volume of a previously selected shot.

\* \* \* \* \*